United States Patent
Landscheidt et al.

Patent Number: 5,886,232
Date of Patent: *Mar. 23, 1999

[54] PROCESS FOR PREPARING SUBSTITUTED CYCLOHEXANONES

[75] Inventors: Heinz Landscheidt, Duisburg; Alexander Klausener; Eberhard Zirngiebl, both of Köln; Wolfgang Kiel, Odenthal, all of Germany

[73] Assignee: Bayer Aktiengesellschaft, Leverkusen, Germany

[*] Notice: This patent issued on a continued prosecution application filed under 37 CFR 1.53(d), and is subject to the twenty year patent term provisions of 35 U.S.C. 154(a)(2).

[21] Appl. No.: 608,651

[22] Filed: Feb. 29, 1996

[30] Foreign Application Priority Data

Mar. 6, 1995 [DE] Germany ............. 195 07 752.0

[51] Int. Cl.⁶ .................................. C07C 45/00
[52] U.S. Cl. ............................ 568/322; 564/169
[58] Field of Search ............... 568/322; 564/109

[56] References Cited

U.S. PATENT DOCUMENTS

| | | |
|---|---|---|
| 2,829,166 | 4/1958 | Joris et al. . |
| 3,124,614 | 3/1964 | Dankert et al. . |
| 3,193,584 | 7/1965 | Rylander et al. . |
| 3,965,180 | 6/1976 | Lednicer . |
| 4,503,273 | 3/1985 | Mozdzen . |

FOREIGN PATENT DOCUMENTS

| | | |
|---|---|---|
| 0186087A1 | 7/1986 | European Pat. Off. . |
| 0186087B1 | 7/1986 | European Pat. Off. . |
| 2752291 | 6/1978 | Germany . |
| 2909780 | 9/1980 | Germany . |
| 189403 | 5/1937 | Switzerland . |
| 1563044 | 3/1980 | United Kingdom . |

OTHER PUBLICATIONS

Chemical Abstracts, vol. 92, abstract No. 58278n, abstract of Zh. Prikl. Khim., vol. 52(8), pp. 1823–1826, (1980).
M. Haslanger, et al., Synthetic Communications, vol. 4(3), pp. 155–159, (1974).
Alicyclics, vol. 96, abstract No. 199167v, abstract of JP 82–04,932, (1982).

*Primary Examiner*—Samuel Barts
*Attorney, Agent, or Firm*—Sprung Kramer Schaefer & Briscoe

[57] ABSTRACT

Substituted cyclohexanones of the formula

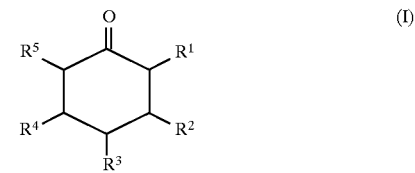

(I)

where
$R^1$ to $R^5$ are as defined in the description, can be obtained by catalytic hydrogenation of phenols of the formula

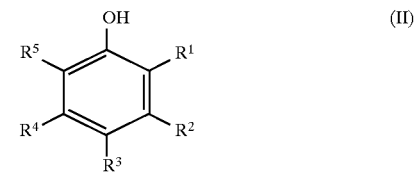

(II)

where
$R^1$ to $R^5$ are as defined in the description.

The reaction is carried out at from 20° to 250° C., from 1 to 200 bar and in an ether as solvent. If desired, an alkaline alkali metal, alkaline earth metal or ammonium compound is used as additive.

7 Claims, No Drawings

PROCESS FOR PREPARING SUBSTITUTED CYCLOHEXANONES

The present invention relates to a process for preparing substituted cyclohexanones by catalytic hydrogenation of the parent substituted phenols in a solvent selected from the group consisting of ethers.

Substituted cyclohexanones are important as intermediates for the preparation of dyes, pharmaceutical active compounds and crop protection agents. Thus, according to U.S. Pat. No. 3,965,180, a pharmaceutically active compound can be synthesized in a few steps starting from 4-hydroxy-cyclohexanone; EP 186 087 describes the preparation of a compound having pharmacological properties, starting from 4-acetylamino-cyclohexanone.

The preparation of the said substituted cyclohexanones according to the prior art is generally carried out in a series of successive synthetic steps. Such processes have the high requirement of chemicals and apparatus and are therefore, in general, to be considered unfavourable from ecological and economic points of view. Thus, Synth. Comm. 4 (1974), pp. 155–159 describes the preparation of 4-hydroxy-cyclohexanone by oxidation of 1,4-cyclohexanediol with chromic acid, a space yield of only 10 g/l being achieved. This low space-time yield, combined with the heavy metal problems, does not allow this process to be used in industry.

It has long been known that unsubstituted cyclohexanone can be prepared in the melt by heterogeneously catalyzed hydrogenation of phenol (U.S. Pat. No. 2,829,166; DE 2 752 291). However, the transfer of this procedure to substituted phenols has succeeded in only a few cases and with frequently unsatisfactory selectivities and yields. Thus, DE 2 909 780 describes, for the example of the preparation of 4-tert-amyl-cyclohexanone from 4-tert-amyl-phenol, the heterogeneously catalyzed hydrogenation of 4-alkylphenols to 4-alkyl-cyclohexanones in the melt. Since the successful carrying out of this reaction requires a reaction temperature in a temperature range from 140° to 200° C. which is favourable for selective hydrogenation, only substituted phenols having a correspondingly low melting point are suitable for such a process. Further restrictions result from the fact that substituted phenols bearing sensitive groups can undergo secondary reactions at the temperatures necessary for working in the melt.

JP 82 004 932 (cited according to C. A. 96: 199 167v) describes the heterogeneously catalyzed hydrogenation of substituted phenols in aqueous solution. However, this gives only extremely low space-time yields which are uninteresting from economic points of view. Thus, in the patent examples, 50 mmol of substituted phenol are reacted in 200 ml of water. A further serious disadvantage of such a procedure results from the fact that the desired reaction product can only be separated from the reaction mixture by complicated extraction with an organic solvent which in the case of industrial implementation leads to a high additional expense.

Apart from the heterogeneously catalyzed hydrogenations in the melt or in aqueous solution cited above by way of example, other solvents have also been used. However, if the directions given in the literature (JP 82/004, 932) are followed, this procedure is likewise associated with disadvantages, since the heterogeneously catalyzed hydrogenation of substituted phenols generally gives a poor selectivity in respect of the desired substituted cyclohexanone. Thus, the comparative examples of the abovementioned patent application demonstrates that conventional organic solvents, such as ethanol or acetic acid, are completely unsuitable.

Similar observations have also been described in various scientific articles. Thus, Zh. Prikl. Khim. 52 (1979) 1823–6 (cited according to C.A. 92: 58 278n) states that in the hydrogenation of 4-tert-butylphenol the yield of ketone drops if the reaction is carried out in a solvent. As the authors assume, the presence of the solvent prevents the association of the phenol with the ketone, as a result of which the latter can be further hydrogenated to give the alcohol.

It was therefore an object of the present invention to find a process which makes possible the hydrogenation of substituted phenols to give substituted cyclohexanones in high yields, selectivities and space-time yields.

The invention provides a process for preparing substituted cyclohexanones of the formula

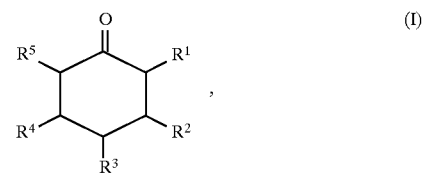

in which
$R^1$, $R^2$, $R^3$, $R^4$ and $R^5$ are, independently of one another, hydrogen, $C_1$–$C_4$-alkyl, $C_3$–$C_8$-cycloalkyl, halogen, hydroxy, $C_1$–$C_4$-alkoxy, $C_3$–$C_8$-cycloalkoxy, $C_1$–$C_4$-alkylamino, $N(C_1$–$C_4$-alkyl$)_2$, —NH—$C_1$–$C_4$-acyl, COOH, COO$C_1$–$C_4$-alkyl or —CH$_2$—Q, where Q represents hydroxy, $C_1$–$C_4$-alkoxy or NH—$C_1$–$C_4$-acyl and where at least one substituent is not hydrogen, by heterogeneously catalyzed hydrogenation of substituted phenols of the formula

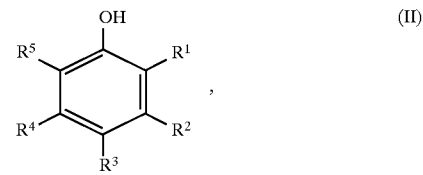

where
$R^1$, $R^2$, $R^3$, $R^4$ and $R^5$ are as defined above,
which is characterized in that the hydrogenation is carried out in the presence of a catalyst, optionally applied to a support, selected from among the metals of group VIIIB of the Periodic Table of the Elements (Mendeleev) and also optionally in the presence of one or more further additives selected from among the alkaline alkali metal, alkaline earth metal or ammonium salts in an ether as solvent.

Halogen is, for example, fluorine, chlorine, bromine, preferably chlorine.

$C_1$–$C_4$-Alkyl is, for example, methyl, ethyl, propyl, isopropyl, butyl, isobutyl, sec-butyl or tert-butyl, preferably methyl or ethyl, particularly preferably methyl.

$C_1$–$C_4$-alkoxy is, for example, methoxy, ethoxy, propoxy, isopropoxy, butoxy, isobutoxy, sec-butoxy or tert-butoxy, preferably methoxy or ethoxy, particularly preferably methoxy.

$C_3$–$C_8$-Cycloalkyl is, for example, cyclopropyl, cyclobutyl, cyclopentyl, cyclohexyl, cycloheptyl, cyclooctyl, monomethyl-, dimethyl-, trimethyl- or tetramethyl-substituted cycloalkyl of the said type having a total of up to 8 carbon atoms or correspondingly ethyl-substituted cycloalkyl, preferably cyclopropyl, cyclopentyl, cyclohexyl or methyl- or ethyl-substituted derivatives thereof.

$C_3$–$C_8$-Cycloalkoxy is derived from the said cycloalkyl in a similar manner to alkoxy from alkyl.

$C_1$–$C_4$-Acyl is, for example, formyl, acetyl, propionyl, n-butyryl or i-butyryl, preferably acetyl.

Preference is given to using a phenol of the formula

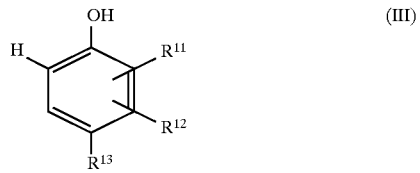

where
$R^{11}$ and $R^{12}$ are, independently of one another, hydrogen, $C_1$–$C_4$-alkyl, $C_1$–$C_4$-alkoxy, chlorine or hydroxy and
$R^{13}$ represents hydroxy, $C_1$–$C_4$-alkyl, $C_1$–$C_4$-alkoxy, $C_1$–$C_4$-alkylamino, $N(C_1$–$C_4$-alkyl$)_2$, NH—$C_1$–$C_4$-acyl or —COO—$C_1$–$C_4$-alkyl.

Particular preference is given to using a phenol of the formula

where
$R^{23}$ is hydroxyl, methoxy, ethoxy, methylamino, dimethylamino or acetamido.

To carry out the process of the present invention, the substituted phenol (II) is dissolved in or mixed with an ether as solvent, in particular in diethylene glycol dimethyl ether, ethylene glycol dimethyl ether, dioxane or tetrahydrofuran, in a weight ratio of from 2:1 to 1:10 (phenol/solvent), optionally at elevated temperature, and admixed with a catalyst, optionally applied to a solid support material such as activated carbon, $Al_2O_3$, $SiO_2$, etc., selected from among the metals of group VIIIB of the Periodic Table of the Elements (Mendeleev) in a weight ratio of from 10,000:1 to 10:1 (phenol/catalyst) and optionally with an additive in a ratio of from 20,000:1 to 20:1 (phenol/activator).

Metals of group VIIIB of the Periodic Table are, for example, palladium, ruthenium, rhodium, platinum, nickel, preferably palladium. Preference is given to using palladium on a support, particularly preferably on activated carbon.

Alkaline salts which can be used as additives are, for example, the hydroxides, hydrides, carbonates, hydrogen carbonates, sulphites, sulphides, phosphates, hydrogen phosphates, borohydrides, borates, $C_1$–$C_6$-carboxylates of Li, Na, K, Rb, Cs, Mg, Ca, Sr, Ba, $NH_4^+$ or substituted $NH_4^+$, preferably the carbonates, hydrogen carbonates, borates, formates and acetates of Na, K, Ca, Mg, e.g. sodium carbonate and borax.

The hydrogenation of the present invention is carried out while stirring at a temperature of from 20° C. to 250° C., preferably from 60° to 230° C., particularly preferably from 100° to 210° C. and at a hydrogen pressure of from 1 bar to 200 bar, preferably from 2 to 150 bar, particularly preferably from 3 to 100 bar. To achieve the optimum selectivity in the hydrogenation, the amount of hydrogen consumed is advantageously recorded so as to be able to stop the hydrogenation on reaching the previously calculated amount of hydrogen of from 1.5 to 2.5 mol of hydrogen per mol of phenol. This can be achieved by lowering the stirrer speed, dropping the temperature and/or interrupting the supply of hydrogen.

After the hydrogenation of the present invention is complete, the catalyst is separated off by means of conventional techniques, for example by filtration.

The solvent can likewise be separated off by means of conventional techniques, for example by distillation, and can, if desired, be recycled. The product can be purified in a manner known per se, for instance by distillation or crystallization.

In principle, it is also possible and may be advantageous to use the solution obtained after completion of the hydrogenation of the present invention and separation of the catalyst directly, i.e. without further work-up, for downstream reactions such as, for example, acetal formation, oxime formation, etc.

EXAMPLES

Example 1

A mixture of 150 g of hydroquinone and 150 ml of diethylene glycol dimethyl ether was hydrogenated at 160° C. and a pressure of 10 bar in the presence of 3 g of Pd (5% by weight) on activated carbon and with addition of 0.5 g of borax. After absorption of 90 l of hydrogen, the hydrogenation was interrupted. Gas-chromatographic analysis indicated formation of 4-hydroxy-cyclohexanone in a selectivity of 80%. Distillation allowed pure 4-hydroxy-cyclohexanone to be obtained in an amount of 65% of the theoretical yield.

Example 2

A mixture of 150 g of 4-methoxyphenol and 150 ml of diethylene glycol dimethyl ether was hydrogenated at 160° C. and a pressure of 10 bar in the presence of 3 g of Pd (5% by weight) on activated carbon and with addition of 0.5 g of borax. After absorption of 90 l of hydrogen, the hydrogenation was interrupted. Gas-chromatographic analysis indicated formation of 4-methoxycyclohexanone in a selectivity of 80%. Distillation allowed pure 4-methoxycyclohexanone to be obtained in an amount of 67% of the theoretical yield.

Example 3

A mixture of 150 g of 4-acetamidophenol and 150 ml of diethylene glycol dimethyl ether was hydrogenated at 160° C. and a pressure of 10 bar in the presence of 3 g of Pd (5% by weight) on activated carbon and with addition of 0.5 g of borax. After absorption of 90 l of hydrogen, the hydrogenation was interrupted. Gas-chromatographic analysis indicated formation of 4-acetamidocyclohexanone in a selectivity of 80%. On cooling the reaction mixture, the product crystallized and could be obtained in an amount of 70% of the theoretical yield.

What is claimed is:

1. A process for preparing a substituted cyclohexanone of the formula

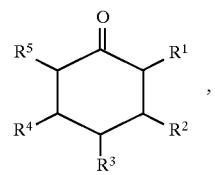

in which
$R^1$, $R^2$, $R^4$ and $R^5$ are hydrogen and $R^3$ is hydroxy, methoxy or acylamino,
by a heterogeneously catalyzed hydrogenation of a substituted phenol of the formula

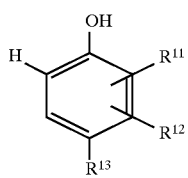

where

R[11] and R[12] are hydrogen and

R[13] is hydroxy, methoxy or acylamino, in which the hydrogenation is carried out at a pressure of 3 to 10 bar in the presence of a catalyst selected from the metals of group VIIIB of the Periodic Table of the Elements (Mendeleev), said catalyst containing a salt selected from the group consisting of alkali metal, alkaline earth metal and ammonium salts, and in an ether as solvent and wherein the hydrogenation is stopped once 1.5 to 2.5 mols of hydrogen per mol of phenol are consumed.

2. The process of claim 1, in which the catalyst is applied to a support.

3. The process of claim 1, in which the hydrogenation is carried out in diethylene glycol dimethyl ether, ethylene glycol dimethyl ether, 1,4-dioxane, tetrahydrofuran or a mixture of a plurality thereof.

4. The process of claim 1, in which the hydrogenation is carried out in a temperature range from 20° C. to 250° C.

5. The process of claim 1, in which the hydrogenation is carried out in a pressure range from 1 bar to 200 bar.

6. The process of claim 1, in which the catalyst used is palladium applied to a support.

7. The process of claim 1, in which an additive is used selected from sodium carbonate and borax.

* * * * *